(12) United States Patent
Moll et al.

(10) Patent No.: US 12,133,737 B2
(45) Date of Patent: Nov. 5, 2024

(54) CARDIOVASCULAR IMPLANTABLE ELECTRONIC DEVICE (CIED) WITH CARDIAC EVENT PREDICTION

(71) Applicant: KØBENHAVNS UNIVERSITET, Copenhagen K (DK)

(72) Inventors: Jonas Jermiin Ravn Moll, Frederiksberg C (DK); Tariq Osman Andersen, Copenhagen K (DK); Christian Igel, Copenhagen K (DK)

(73) Assignee: KØBENHAVNS UNIVERSITET, Copenhagen K (DK)

( * ) Notice: Subject to any disclaimer, the term of this patent is extended or adjusted under 35 U.S.C. 154(b) by 0 days.

(21) Appl. No.: 17/059,646

(22) PCT Filed: May 9, 2019

(86) PCT No.: PCT/EP2019/061925
§ 371 (c)(1),
(2) Date: Nov. 30, 2020

(87) PCT Pub. No.: WO2019/228775
PCT Pub. Date: Dec. 5, 2019

(65) Prior Publication Data
US 2021/0204859 A1  Jul. 8, 2021

(30) Foreign Application Priority Data
May 31, 2018  (DK) .................................. 201800246

(51) Int. Cl.
*A61B 5/00* (2006.01)
*A61B 5/024* (2006.01)
(Continued)

(52) U.S. Cl.
CPC .............. *A61B 5/361* (2021.01); *A61B 5/024* (2013.01); *A61B 5/363* (2021.01); *A61B 5/686* (2013.01); *A61B 5/746* (2013.01); *A61N 1/0563* (2013.01)

(58) Field of Classification Search
CPC ......... A61B 5/361; A61B 5/024; A61B 5/363; A61B 5/686; A61B 5/746; A61B 5/4836;
(Continued)

(56) References Cited

U.S. PATENT DOCUMENTS

2002/0016550 A1 *  2/2002  Sweeney ................. G16Z 99/00
                                                        600/515
2002/0120306 A1     8/2002  Zhu et al.
(Continued)

FOREIGN PATENT DOCUMENTS

WO          200805480 A       5/2008

OTHER PUBLICATIONS

International Search Report and Written Opinion mailed on Jul. 23, 2019 for PCT/EP2019/061925 filed on May 9, 2019, 12 pages including English Translation of the International Search Report.
(Continued)

*Primary Examiner* — Scott M. Getzow
(74) *Attorney, Agent, or Firm* — XSENSUS LLP

(57) ABSTRACT

A cardiovascular implantable electronic device (CIED) and related method is disclosed. The CIED comprises a first lead for cardiac stimulation; one or more sensors for provision of sensor data; and a processing device comprising a processor, a communication interface and a lead interface. The the processor is configured to: obtain sensor data from the one or more sensors; determine a first set of first parameters based on the sensor data; determine a second set of second parameters based on the sensor data; determine a first cardiac event parameter indicative of a probability of a
(Continued)

future cardiac event, wherein the first cardiac event parameter is based on one or more parameters of the first set and the second set; determine if one or more transmission criteria are satisfied; and, if so, transmit a first warning signal to an accessory device, the first warning signal being indicative of the first cardiac event parameter.

19 Claims, 6 Drawing Sheets

(51) Int. Cl.
*A61B 5/361* (2021.01)
*A61B 5/363* (2021.01)
*A61N 1/05* (2006.01)

(58) Field of Classification Search
CPC .. A61B 5/7275; A61N 1/0563; A61N 1/3956; A61N 1/365
See application file for complete search history.

(56) References Cited

U.S. PATENT DOCUMENTS

| | | | |
|---|---|---|---|
| 2005/0137489 A1* | 6/2005 | Jackson | A61B 5/02438 600/515 |
| 2008/0139954 A1* | 6/2008 | Day | A61N 1/3956 600/523 |
| 2009/0275848 A1 | 11/2009 | Brockway et al. | |
| 2010/0152802 A1 | 6/2010 | Min | |
| 2011/0224565 A1* | 9/2011 | Ong | A61B 5/7275 600/509 |
| 2011/0301479 A1 | 12/2011 | Ghanem et al. | |
| 2012/0271177 A1 | 10/2012 | Emerson et al. | |
| 2013/0079861 A1 | 3/2013 | Reinert et al. | |
| 2016/0135706 A1* | 5/2016 | Sullivan | A61B 5/316 600/509 |
| 2017/0035297 A1 | 2/2017 | Hatlestad et al. | |

OTHER PUBLICATIONS

Danish Patent and Trademark Office 1st Technical Examination Report dated Nov. 27, 2018, pp. 1-10.

* cited by examiner

CARDIOVASCULAR IMPLANTABLE ELECTRONIC DEVICE (CIED) WITH CARDIAC EVENT PREDICTION

CROSS-REFERENCE TO RELATED APPLICATIONS

The present application is based on PCT filing PCT/EP2019/061925, filed May 9, 2019, which claims priority to PA201800246, filed May 31, 2018, the entire contents of each are incorporated herein by reference.

The present disclosure relates to a cardiovascular implantable electronic device (CIED) with cardiac event prediction and related method, in particular a method for cardiac event prediction.

BACKGROUND

Cardiac events, such as strokes and cardiac arrests are life-threatening and arise from severe cardiac arrhythmias such as atrial fibrillation, ventricular fibrillation and electrical storm. Today, cardiac events can be detected and/or treated with cardiovascular implantable electronic devices (CIED) such as pacemakers, ICDs, CRTDs, and implantable loop recorders. However, current solutions merely allow to react to cardiac events when they have already occurred.

SUMMARY

Thus, there is a need for devices and methods enabling a more effective and efficient monitoring of cardiac patients. Further, there is need for methods and/or devices to determine with a high degree of certainty the risk of a cardiac event in order to intervene/take the necessary steps to handle the event.

Accordingly, a cardiovascular implantable electronic device is provided, the cardiovascular implantable electronic device comprising a first lead for cardiac stimulation; one or more sensors for provision of sensor data; and a processing device comprising a processor, a communication interface, and a lead interface. The processor is configured to obtain sensor data from the one or more sensors and determine one or more sets of parameters, such as one or more sets of a first set of first parameter(s), a second set of second parameter(s), a third set of third parameter(s), and a fourth set of fourth parameter(s), based on the sensor data. The processor is configured to determine one or more cardiac event parameters including a first cardiac event parameter indicative of a probability of a future cardiac event, such as a first cardiac event, and optionally indicative of a probability of a first cardiac event occurring within a first time period of 15 minutes to 1 week, wherein the first cardiac event parameter is based on one or more parameters of the one or more sets of parameters, such as one or more of first parameter(s) of the first set, second parameter(s) of the second set, third parameter(s) of the third set, and fourth parameter(s) of the fourth set. The processor is configured to determine if one or more transmission criteria are satisfied; and in accordance with a first transmission criterion being satisfied, transmit a first warning signal to an accessory device. The first warning signal may be indicative of the first cardiac event parameter.

Also disclosed is a method, optionally performed in a cardiovascular implantable electronic device, for cardiac event prediction, the method comprising obtaining sensor data from one or more sensors of the cardiovascular implantable electronic device, and determining one or more sets of parameters, such as one or more sets of a first set of first parameter(s), a second set of second parameter(s), a third set of third parameter(s), and a fourth set of fourth parameter(s), based on the sensor data. The method comprises determining one or more cardiac event parameters including a first cardiac event parameter indicative of a probability of a future cardiac event, such as a first cardiac event, and optionally indicative of a probability of a first cardiac event occurring within a first time period of 15 minutes to 1 week, wherein the first cardiac event parameter is based on one or more parameters of the one or more of sets of parameters, such as one or more of first parameter(s) of the first set, one or more second parameter(s) of the second set, one or more third parameter(s) of the third set, and one or more fourth parameter(s) of the fourth set; determining if one or more transmission criteria are satisfied; and in accordance with a first transmission criterion being satisfied, transmitting a first warning signal to an accessory device. The first warning signal may be indicative of the first cardiac event parameter.

It is an advantage of the present disclosure that cardiac events are predicted and clinician/patient is alerted about cardiac events before they happen. This is very different and more effective than current state-of-the-art where treatment happens at the time or after the dangerous arrhythmias have been detected. Short-term prediction of worsening is a major change in the way clinical decision-making in CIED remote monitoring is carried out today. Ultimately, the present disclosure is intended to reduce the number of strokes and life-threatening cardiac arrests by making a clinical intervention possible before the dangerous arrhythmias happen. Short-term prediction of severe cardiac events improves the quality of care and the quality of life of heart patients.

It is an important advantage of the present disclosure that the occurrence of future cardiac events can be predicted up to a week in advance, thereby allowing sufficient time for the patient and/or clinician to take proper measures, e.g. to prepare for the cardiac event and/or take appropriate prophylactic measures, in order to reduce the risk of occurrence of the cardiac event or actually avoiding the cardiac event. Further, the risk of side effects resulting from the cardiac events, e.g. traffic accidents, damages to the patient, for example due to the patient falling or passing out, can be heavily reduced.

Further, a power-efficient CIED is provided by controlling transmission from the CIED, while appropriately informing the patient/clinician or cardiac monitoring system about the current status of the patient.

The disclosed system and method provide improved clinical decision-making in remote monitoring and/or increased patient satisfaction through improved communication. The disclosed device and method advantageously guides and automates the communication from the CIED in turn providing the CIED patient and/or clinician with an improved and more accurate tool for cardiac monitoring.

The present disclosure supports a user in reducing the risk of cardiac events that can lead to cardiac arrest. Further, a CIED with efficient power management is provided.

BRIEF DESCRIPTION OF THE DRAWINGS

The above and other features and advantages of the present disclosure will become readily apparent to those skilled in the art by the following detailed description of exemplary embodiments thereof with reference to the attached drawings, in which.

DETAILED DESCRIPTION

Figure 1:
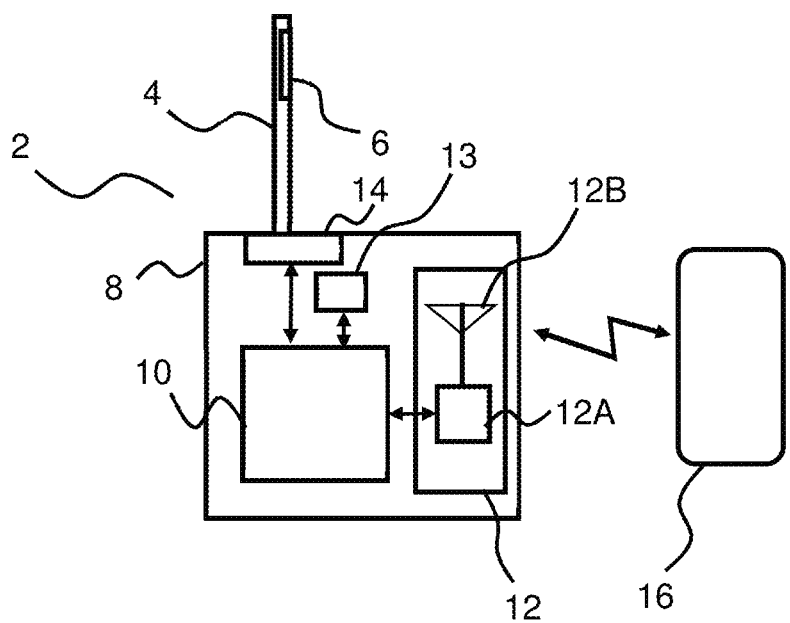
FIG. 1 schematically illustrates an exemplary cardiovascular implantable electronic device and an accessory device.

The present disclosure relates to a cardiovascular implantable electronic device (CIED) with cardiac event prediction and related method.

The CIED may be or comprise an Implantable Cardioverter Defibrillator (ICD), a Cardiac Resynchronization Therapy device (CRT-D), a Cardiac Resynchronization Therapy Pacemaker (CRT-P) or an Implantable Loop Recorder (ILR). The accessory device may be a smartphone.

In the present context, electrical storm (ES) is defined as the occurrence of three or more episodes of ventricular arrhythmias including VT and VF events treated by device electrical therapy (appropriate anti-tachycardia pacing and/or shock delivery) within a 24 h period.

The cardiovascular implantable electronic device (CIED) comprises a first lead for cardiac stimulation and one or more sensors for provision of sensor data. A first sensor of the one or more sensors may be arranged in the first lead. The CIED may comprise a second sensor. The second sensor may be arranged in the processing device. The sensor data may comprise first sensor data of a first sensor and/or second sensor data of a second sensor. The CIED comprises a power supply, such as a rechargeable battery.

The CIED comprises a processing device comprising a processor, a communication interface and a lead interface. The first lead is connected to the processing device via the lead interface. The processor is connected to the one or more sensors and configured to obtain sensor data from the one or more sensors.

The processor is configured to determine a first set of first parameters based on the sensor data and/or a second set of second parameters based on the sensor data.

A set of parameters, such as the first set of first parameters may comprise one or more parameters, such as one or more of a primary parameter, a secondary parameter, a tertiary parameter, and a quaternary parameter.

A primary parameter may be based on sensor data of a primary time window. A primary parameter may be based on sensor data during an event, such as Ventricular Tachycardia or Ventricular Fibrillation. The primary time window may be current day, i.e. a primary parameter may be based on sensor data of the current day (CD). The primary time window may be daytime of current day. The primary time window may be night-time of current day.

A secondary parameter may be based on sensor data of a secondary time window. A secondary parameter may be based on sensor data during an event, such as Ventricular Tachycardia or Ventricular Fibrillation. The secondary time window may be current day-1, i.e. a secondary parameter may be based on sensor data of yesterday. The secondary time window may be daytime of current day-1. The secondary time window may be night-time of current day-1.

A tertiary parameter may be based on sensor data of a tertiary time window. A tertiary parameter may be based on sensor data during an event, such as Ventricular Tachycardia or Ventricular Fibrillation. The tertiary time window may be current day-2, i.e. a tertiary parameter may be based on sensor data of the day before yesterday (two days ago). The tertiary time window may be daytime of current day-2. The tertiary time window may be night-time of current day-2.

A quaternary parameter may be based on sensor data of a quaternary time window. A quaternary parameter may be based on sensor data during an event, such as Ventricular Tachycardia or Ventricular Fibrillation. The quaternary time window may be current day-3, i.e. a quaternary parameter may be based on sensor data of three days ago. The quaternary time window may be daytime of current day-3. The quaternary time window may be night-time of current day-3.

The processor may be configured to determine a first set of first parameters based on the sensor data. The first set of first parameters may comprise one, two, three, four or more first parameters. The first set of first parameters may comprise at least three first parameters. The first set $P\_1$ of first parameters may comprise a first primary parameter, also denoted $p\_1\_1$, and/or a first secondary parameter, also denoted $p\_1\_2$. The first set $P\_1$ of first parameters may comprise a first tertiary parameter, also denoted $p\_1\_3$. The first set $P\_1$ of first parameters may comprise a first quaternary parameter, also denoted $p\_1\_4$.

The first parameter(s) may be indicative of activity of the patient/user, i.e. the first parameter(s) may be indicative of the patient's level of activity during a time period, such as a day, daytime, or night-time.

The first parameter(s) may be indicative of an average heart rate of the patient/user, e.g. during a time period, such as a day, daytime, or night-time. The first parameter(s) may be indicative of an average heart rate of the patient/user during daytime. The first parameter(s) may be indicative of an average heart rate of the patient/user during night-time.

The first parameter(s) may be indicative of a heart rate variability of the patient/user, e.g. during a time period, such as a day, daytime, or night-time.

The first parameter(s) may be indicative of an average heart rate of the patient/user, e.g. during a time period, such as a day, daytime, or night-time.

The first parameter(s) may be indicative of a heart rate of the patient/user, e.g. during an event, such as Ventricular Tachycardia or Ventricular Fibrillation.

The processor may be configured to determine or obtain a second set of second parameters based on the sensor data. The second set of second parameters may comprise one, two, three, four or more second parameters. The second set of second parameters may comprise at least three second parameters. The second set $P\_2$ of second parameters may comprise a second primary parameter, also denoted $p\_2\_1$, and/or a second secondary parameter, also denoted $p\_2\_2$. The second set $P\_2$ of second parameters may comprise a second tertiary parameter, also denoted $p\_2\_3$. The second set $P\_2$ of second parameters may comprise a second quaternary parameter, also denoted $p\_2\_4$.

The second parameter(s) may be indicative of activity of the patient/user, i.e. the second parameter(s) may be indicative of the patient's level of activity during a time period, such as a day, daytime, or night-time.

The second parameter(s) may be indicative of an average heart rate of the patient/user, e.g. during a time period, such as a day, daytime, or night-time. The second parameter(s) may be indicative of an average heart rate of the patient/user during daytime. The second parameter(s) may be indicative of an average heart rate of the patient/user during night-time.

The second parameter(s) may be indicative of a heart rate variability of the patient/user, e.g. during a time period, such as a day, daytime, or night-time.

The second parameter(s) may be indicative of an average heart rate of the patient/user, e.g. during a time period, such as a day, daytime, or night-time.

The second parameter(s) may be indicative of a heart rate of the patient/user, e.g. during an event, such as Ventricular Tachycardia or Ventricular Fibrillation.

The processor may be configured to determine or obtain a third set of third parameters based on the sensor data. The third set of third parameters may comprise one, two, three, four or more third parameters. The third set of third parameters may comprise at least three third parameters. The third set $P\_3$ of third parameters may comprise a third primary parameter, also denoted $p\_3\_1$, and/or a third secondary parameter, also denoted $p\_3\_2$. The third set $P\_3$ of third parameters may comprise a third tertiary parameter, also denoted $p\_3\_3$. The third set $P\_3$ of third parameters may comprise a third quaternary parameter, also denoted $p\_3\_4$.

The third parameter(s) may be indicative of activity of the patient/user, i.e. the third parameter(s) may be indicative of the patient's level of activity during a time period, such as a day, daytime, or night-time.

The third parameter(s) may be indicative of an average heart rate of the patient/user, e.g. during a time period, such as a day, daytime, or night-time. The third parameter(s) may be indicative of an average heart rate of the patient/user during daytime. The third parameter(s) may be indicative of an average heart rate of the patient/user during night-time.

The third parameter(s) may be indicative of a heart rate variability of the patient/user, e.g. during a time period, such as a day, daytime, or night-time.

The third parameter(s) may be indicative of an average heart rate of the patient/user, e.g. during a time period, such as a day, daytime, or night-time.

The third parameter(s) may be indicative of a heart rate of the patient/user, e.g. during an event, such as Ventricular Tachycardia or Ventricular Fibrillation.

The processor may be configured to determine or obtain a fourth set of fourth parameters based on the sensor data. The fourth set of fourth parameters may comprise one, two, three, four or more fourth parameters. The fourth set of fourth parameters may comprise at least three fourth parameters. The fourth set $P\_4$ of fourth parameters may comprise a fourth primary parameter, also denoted $p\_4\_1$, and/or a fourth secondary parameter, also denoted $p\_4\_2$. The fourth set $P\_4$ of fourth parameters may comprise a fourth tertiary parameter, also denoted $p\_4\_3$. The fourth set $P\_4$ of fourth parameters may comprise a fourth quaternary parameter, also denoted $p\_4\_4$.

The fourth parameter(s) may be indicative of activity of the patient/user, i.e. the fourth parameter(s) may be indicative of the patient's level of activity during a time period, such as a day, daytime, or night-time.

The fourth parameter(s) may be indicative of an average heart rate of the patient/user, e.g. during a time period, such as a day, daytime, or night-time. The fourth parameter(s) may be indicative of an average heart rate of the patient/user during daytime. The fourth parameter(s) may be indicative of an average heart rate of the patient/user during night-time.

The fourth parameter(s) may be indicative of a heart rate variability of the patient/user, e.g. during a time period, such as a day, daytime, or night-time.

The fourth parameter(s) may be indicative of an average heart rate of the patient/user, e.g. during a time period, such as a day, daytime, or night-time.

The fourth parameter(s) may be indicative of a heart rate of the patient/user, e.g. during an event, such as Ventricular Tachycardia or Ventricular Fibrillation.

The processor may be configured to determine or obtain a fifth set of fifth parameters based on the sensor data. The fifth set of fifth parameters may comprise one, two, three, four or more fifth parameters. The fifth set of fifth parameters may comprise at least three fifth parameters. The fifth set $P\_5$ of fifth parameters may comprise a fifth primary parameter, also denoted $p\_5\_1$, and/or a fifth secondary parameter, also denoted $p\_5\_2$. The fifth set $P\_5$ of fifth parameters may comprise a fifth tertiary parameter, also denoted $p\_5\_3$. The fifth set $P\_5$ of fifth parameters may comprise a fifth quaternary parameter, also denoted $p\_5\_4$.

The fifth parameter(s) may be indicative of activity of the patient/user, i.e. the fifth parameter(s) may be indicative of the patient's level of activity during a time period, such as a day, daytime, or night-time.

The fifth parameter(s) may be indicative of an average heart rate of the patient/user, e.g. during a time period, such as a day, daytime, or night-time. The fifth parameter(s) may be indicative of an average heart rate of the patient/user during daytime. The fifth parameter(s) may be indicative of an average heart rate of the patient/user during night-time.

The fifth parameter(s) may be indicative of a heart rate variability of the patient/user, e.g. during a time period, such as a day, daytime, or night-time.

The fifth parameter(s) may be indicative of an average heart rate of the patient/user, e.g. during a time period, such as a day, daytime, or night-time.

The fifth parameter(s) may be indicative of a heart rate of the patient/user, e.g. during an event, such as Ventricular Tachycardia or Ventricular Fibrillation.

The processor is configured to determine one or more cardiac event parameters including a first cardiac event parameter. The processor is optionally configured to determine a first cardiac event parameter indicative of a probability of a future cardiac event. The first cardiac event parameter, also denoted $P\_CE\_1$, may be based on one or more first parameters of the first set of first parameter(s). Thus, $P\_CE\_1$ may be a function of $P\_1$ or at least parts thereof. The first cardiac event parameter, also denoted $P\_CE\_1$, may be based on one or more second parameters of the second set of second parameter(s). Thus, $P\_CE\_1$ may be a function of $P\_2$ or at least parts thereof. The first cardiac event parameter, also denoted $P\_CE\_1$, may be based on one or more third parameters of the third set of third parameter(s). Thus, $P\_CE\_1$ may be a function of $P\_3$ or at least parts thereof. The first cardiac event parameter, also denoted $P\_CE\_1$, may be based on one or more fourth parameters of the fourth set of fourth parameter(s). Thus, $P\_CE\_1$ may be a function of $P\_4$ or at least parts thereof. The first cardiac event parameter, also denoted $P\_CE\_1$, may be based on one or more fifth parameters of the fifth set of fifth parameter(s). Thus, $P\_CE\_1$ may be a function of $P\_5$ or at least parts thereof.

In one or more exemplary CIEDs and/or methods, to determine one or more cardiac event parameters comprises to select a precision parameter and/or a recall parameter, and determine first cardiac event parameter and/or second cardiac event parameter based on the precision parameter and/or a recall parameter. The precision parameter may be in the range from 0 to 1. The recall parameter may be in the range from 0 to 1.

In one or more exemplary CIEDs and/or methods, the first cardiac event parameter is indicative of a probability of a first cardiac event occurring within a first time period of 15 minutes to 1 week.

In one or more exemplary CIEDs and/or methods, the first cardiac event parameter is indicative of a probability of a first cardiac event occurring within a first time period of 0.5 hour to 72 hours. In one or more exemplary CIEDs, the first cardiac event parameter is indicative of a probability of a first cardiac event occurring within a first time period of 1 hour to 24 hours. In one or more exemplary CIEDs, the first cardiac event parameter is indicative of a probability of a first cardiac event occurring within a first time period of 12 hours to 24 hours.

In one or more exemplary CIEDs and/or methods, the first cardiac event parameter is indicative of a probability of a first cardiac event occurring within a first time period of 5 minutes to 15 minutes. In one or more exemplary CIEDs and/or methods, the first cardiac event parameter is indicative of a probability of a first cardiac event occurring within a first time period of 15 minutes to 12 hours.

In one or more exemplary CIEDs and/or methods, the first cardiac event parameter is a logic value (0 or 1), where 1 optionally indicates that a first cardiac event will occur within a first time period and 0 optionally indicates that the first cardiac event will not occur within the first time period.

The processor is configured to determine if one or more transmission criteria are satisfied. The one or more transmission criteria may comprise a first transmission criterion and/or a second transmission criterion. A transmission criterion may comprise one or more logical expressions. The first transmission criterion may be based on the first cardiac event parameter. In one or more exemplary CIEDs and/or methods, the first transmission criterion is satisfied if the first cardiac event parameter is larger than a first threshold, TH_1. The first threshold may be larger than 0.2. The first threshold may be larger than 0.4, such as 0.5, 0.6, 0.7, 0.8, 0.90 or 0.95. In one or more exemplary CIEDs and/or methods, the first threshold is in the range from 0.4 to 0.95. Thus, the first transmission criterion may be based on a first threshold.

The processor may be configured to, in accordance with a first transmission criterion being satisfied, transmit a first warning signal to an accessory device. The first warning signal may be indicative of the first cardiac event parameter.

The processor is configured to determine a first cardiac event parameter indicative of a probability of a future cardiac event. The future cardiac event may be a first cardiac event. The first cardiac event may be electrical storm. Thus, the processor may be configured to determine a first cardiac event parameter indicative of a probability of a future electrical storm. The first cardiac event may be atrial fibrillation. Thus, the processor may be configured to determine a first cardiac event parameter indicative of a probability of future atrial fibrillation. The first cardiac event may be ventricular fibrillation/ventricular tachycardia. Thus, the processor may be configured to determine a first cardiac event parameter indicative of a probability of future ventricular fibrillation/ventricular tachycardia.

The processor may be configured to determine a second cardiac event parameter indicative of a probability of a future cardiac event, wherein the second cardiac event parameter is optionally based on one or more first parameters of the first set. In accordance with a second transmission criterion being satisfied, the processor may be configured to transmit a second warning signal to an accessory device, the second warning signal optionally being indicative of the second cardiac event parameter.

In one or more exemplary CIEDs and/or methods, the second cardiac event parameter is indicative of a probability of the first cardiac event or a second cardiac event occurring within a second time period, e.g. of 15 minutes to 1 week.

In one or more exemplary CIEDs and/or methods, the second cardiac event parameter is indicative of a probability of the first cardiac event or a second cardiac event occurring within a second time period of 0.5 hour to 72 hours. In one or more exemplary CIEDs, the second cardiac event parameter is indicative of a probability of the first cardiac event or a second cardiac event occurring within a second time period of 1 hour to 24 hours. In one or more exemplary CIEDs and/or methods, the second cardiac event parameter is indicative of a probability of the first cardiac event or a second cardiac event occurring within a second time period of 12 hours to 24 hours. The second time period may overlap with the first time period or be separate from (non-overlapping with) the first time period.

In one or more exemplary CIEDs and/or methods, the second cardiac event parameter is a logic value (0 or 1), where 1 optionally indicates that the first cardiac event or a second cardiac event will occur within a second time period and 0 optionally indicates that the first cardiac event or the second cardiac event will not occur within the second time period.

The second transmission criterion may be based on the second cardiac event parameter. In one or more exemplary CIEDs and/or methods, the second transmission criterion is satisfied if the second cardiac event parameter is larger than a second threshold, TH_2. The second threshold may be larger than 0.2. The second threshold may be larger than 0.4, such as 0.5, 0.6, 0.7, 0.8, 0.90 or 0.95. In one or more exemplary CIEDs and/or methods, the second threshold is in the range from 0.4 to 0.95. Thus, the second transmission criterion may be based on a second threshold.

The processor may be configured to determine a second cardiac event parameter indicative of a probability of a future cardiac event, i.e. the one or more cardiac event parameters may include a second cardiac event parameter indicative of a probability of a future cardiac event. The future cardiac event may be the first cardiac event or a second cardiac event. The second cardiac event may be electrical storm. Thus, the processor may be configured to determine a second cardiac event parameter indicative of a probability of a future electrical storm. The second cardiac event may be atrial fibrillation. Thus, the processor may be configured to determine a second cardiac event parameter indicative of a probability of future atrial fibrillation. The second cardiac event may be ventricular fibrillation/ventricular tachycardia. Thus, the processor may be configured to determine a second cardiac event parameter indicative of a probability of future ventricular fibrillation/ventricular tachycardia.

The second cardiac event parameter may be based on one or more second parameters of the second set. The second cardiac event parameter may be based on one or more third parameters of the third set. The second cardiac event parameter may be based on one or more fourth parameters of the fourth set. The second cardiac event parameter may be based on one or more fifth parameters of the fifth set.

A method for cardiovascular event prediction is disclosed, the method comprising: obtaining sensor data from one or more sensors of one or more sensors of the cardiovascular implantable electronic device; determining a first set of first parameters based on the sensor data; determining a second set of second parameters based on the sensor data; determining one or more cardiac event parameters including a first cardiac event parameter indicative of a probability of a future cardiac event, wherein the first cardiac event parameter is based on one or more first parameters of the first set and one or more second parameters of the second set; determining if one or more transmission criteria are satisfied; and in accordance with a first transmission criterion being satisfied, transmitting a first warning signal to an accessory device, the first warning signal being indicative of the first cardiac event parameter. The method may be performed in a cardiovascular implantable electronic device.

The method may comprise determining a second set of second parameters based on the sensor data, and the first cardiac event parameter may be based on one or more second parameters of the second set. The method may comprise determining a third set of third parameters based on the sensor data, and the first cardiac event parameter may be based on one or more third parameters of the third set. The method may comprise determining a fourth set of fourth parameters based on the sensor data, and the first cardiac event parameter may be based on one or more fourth parameters of the fourth set. The method may comprise determining a fifth set of fifth parameters based on the sensor data, and the first cardiac event parameter may be based on one or more fifth parameters of the fifth set.

In the method, determining one or more cardiac event parameters may comprise determining a second cardiac event parameter indicative of a probability of a future cardiac event, such as the first cardiac event or a second cardiac event, wherein the second cardiac event parameter is optionally based on one or more first parameters of the first set; and in accordance with a second transmission criterion being satisfied, transmitting a second warning signal to an accessory device, the second warning signal optionally being indicative of the second cardiac event parameter.

Determination of cardiac event parameter(s), such as the first cardiac event parameter and/or the second cardiac event parameter, may be based on a model, such as logistic regression, random forest, ada boost, deep neural networks or similar. Determination of the second cardiac event parameter may be based on a model, such as logistic regression, random forest, ada boost, deep neural networks or similar. Determination of the first cardiac event parameter may be based on a first model and the second cardiac event parameter may be based on a second model. The first model may be selected from logistic regression, random forest, ada boost and deep neural networks. The first model may be a random forest model. In one or more exemplary CIED's and/or methods, the first model is a random forest model, wherein the random forest model comprises N trees. The number N of trees may be in the range from 50 to 200, such as about 75, 100, 125, 150 or 175. One or more, such as a plurality, of the N trees may each have a maximum depth in the range from 8 to 12. The second model may be selected from logistic regression, random forest, ada boost and deep neural networks. The second model may be a random forest model. The second model may be different from or the same as the first model. Using different models facilitates utilization of an optimum model for different cardiac event parameters. In one or more exemplary CIED's and/or methods, the second model is a random forest model, wherein the random forest model comprises M trees. The number M of trees may be in the range from 50 to 200, such as about 75, 100, 125, 150 or 175. One or more, such as a plurality, of the M trees may each have a maximum depth in the range from 8 to 12.

In one or more exemplary CIEDs and/or methods, cardiac event parameters may be determined once a day, e.g. at the end of the current day. A day denotes a time frame of 24 hours, e.g. starting at midnight. In one or more exemplary CIEDs and/or methods, a day may start at e.g. 22.00 (10 PM).

In one or more exemplary CIEDs and/or methods, the first cardiac event parameter is indicative of a probability of a first cardiac event (VT/VF) occurring within a day (24 hours) and based on at least P_1 and P_2, the first parameters of P_1 are indicative of heart rate during VT/VF, wherein P_1 includes first primary parameter p_1_1 indicative of heart rate during VT/VF current day, first secondary parameter p_1_2 indicative of heart rate during VT/VF yesterday, i.e. CD-1, first tertiary parameter p_1_3 indicative of heart rate during VT/VF two days ago, i.e. CD-2, and first quaternary parameter p_1_4 indicative of heart rate during VT/VF three days ago, i.e. CD-3, and the second parameters of P_2 are indicative of average heart rate during daytime, wherein P_2 includes second tertiary parameter p_2_3 indicative of average heart rate during daytime two days ago, i.e. CD-2, and second quaternary parameter p_2_4 indicative of average heart rate during daytime three days ago, i.e. CD-3. In one or more exemplary CIEDs and/or methods wherein the first cardiac event parameter is indicative of a probability of a first cardiac event (VT/VF) occurring within a day, the first cardiac event parameter may be based on third parameter(s) of P_3, wherein the third parameter(s) of P_3 is/are an activity parameter, i.e. indicative of the patient's level of activity during the day, wherein P_3 includes third tertiary parameter p_3_3 indicative of activity level during daytime two days ago, i.e. CD-2, and/or third quaternary parameter p_3_4 indicative of activity level during daytime three days ago, i.e. CD-3. In one or more exemplary CIEDs and/or methods wherein the first cardiac event parameter is indicative of a probability of a first cardiac event (VT/VF) occurring within a day, the first cardiac event parameter may be based on fourth parameter(s) of P_4, wherein the fourth parameter(s) of P_4 is/are indicative of heart rate variability during the day, wherein P_4 includes fourth tertiary parameter p_4_3 indicative of heart rate variability during the day two days ago, i.e. CD-2, and/or fourth quaternary parameter p_4_4 indicative of heart rate variability during a day three days ago, i.e. CD-3. The first transmission criterion may in this example be satisfied if the first cardiac event parameter P_CE_1>TH_1, wherein the first threshold TH_1 is 0.5, see also FIG. 4 and corresponding description below.

In one or more exemplary CIEDs and/or methods, the first cardiac event parameter is indicative of a probability of a first cardiac event (VT/VF) occurring within a week and based on at least P_1 and optionally P_2, the first parameters of P_1 are indicative of heart rate during VT/VF, wherein P_1 includes first primary parameter p_1_1 indicative of heart rate during VT/VF current day, first secondary parameter p_1_2 indicative of heart rate during VT/VF yesterday, i.e. CD-1, first tertiary parameter p_1_3 indicative of heart rate during VT/VF two days ago, i.e. CD-2, and first quaternary parameter p_1_4 indicative of heart rate during VT/VF three days ago, i.e. CD-3, and the second parameters of P_2 are indicative of average heart rate during daytime, wherein P_2 includes second tertiary parameter p_2_3 indicative of average heart rate during daytime two days ago, i.e. CD-2, and second quaternary parameter p_2_4 indicative of average heart rate during daytime three days ago, i.e. CD-3. In one or more exemplary CIEDs and/or methods wherein the first cardiac event parameter is indicative of a probability of a first cardiac event (VT/VF) occurring within a week, the first cardiac event parameter may be based on third parameter(s) of P_3, wherein the third parameter(s) of P_3 is/are an activity parameter, i.e. indicative of the patient's level of activity during the day, wherein P_3 includes third tertiary parameter p_3_3 indicative of activity level during daytime two days ago, i.e. CD-2, and/or third quaternary parameter p_3_4 indicative of activity level during daytime three days ago, i.e. CD-3. In one or more exemplary CIEDs and/or methods wherein the first cardiac event parameter is indicative of a probability of a first cardiac event (VTNF) occurring within a week, the first cardiac event parameter may be based on fourth parameter(s) of P_4, wherein the fourth parameter(s) of P_4 is/are indicative of average heart rate during nighttime, wherein P_4 includes fourth tertiary parameter p_4_3 indicative of average heart rate during nighttime two days ago, i.e. CD-2, and/or fourth quaternary parameter p_4_4 indicative of average heart rate during nighttime, i.e. CD-3. The first transmission criterion may in this example be satisfied if the first cardiac event parameter P_CE_1>TH_1, wherein the first threshold TH_1 is 0.5, see also FIG. 5 and corresponding description below.

In one or more exemplary CIEDs and/or methods, the first cardiac event parameter is indicative of a probability of a first cardiac event (electrical storm) occurring within a day and based on at least P_1 and optionally P_2, the first parameters of P_1 are indicative of activity, wherein P_1 includes first primary parameter p_1_1 indicative of activity current day, first secondary parameter p_1_2 indicative of activity yesterday, i.e. CD-1, first tertiary parameter p_1_3 indicative of activity two days ago, i.e. CD-2, and first quaternary parameter p_1_4 indicative of activity three days ago, i.e. CD-3, and the second parameters of P_2 are indicative of average heart rate during nighttime, wherein P_2 includes second tertiary parameter p_2_3 indicative of average heart rate during nighttime two days ago, i.e. CD-2, and second quaternary parameter p_2_4 indicative of average heart rate during nighttime three days ago, i.e. CD-3. In one or more exemplary CIEDs and/or methods wherein the first cardiac event parameter is indicative of a probability of a first cardiac event (electrical storm) occurring within a day, the first cardiac event parameter may be based on third parameter(s) of P_3, wherein the third parameter(s) of P_3 is/are indicative of heart rate variability, wherein P_3 includes third tertiary parameter p_3_3 indicative of heart rate variability two days ago, i.e. CD-2, and/or third quaternary parameter p_3_4 indicative of heart rate variability three days ago, i.e. CD-3. In one or more exemplary CIEDs and/or methods wherein the first cardiac event parameter is indicative of a probability of a first cardiac event (electrical storm) occurring within a day, the first cardiac event parameter may be based on fourth parameter(s) of P_4, wherein the fourth parameter(s) of P_4 is/are indicative of heart rate during VT/VF, wherein P_4 includes fourth tertiary parameter p_4_3 indicative of heart rate during VT/VF two days ago, i.e. CD-2, and/or fourth quaternary parameter p_4_4 indicative of heart rate during VT/VF, i.e. CD-3. The first transmission criterion may in this example be satisfied if the first cardiac event parameter P_CE_1>TH_1, wherein the first threshold TH_1 is 0.5.

FIG. 1 schematically illustrates an exemplary CIED according to the present disclosure with CIED 2 comprising a first lead 4 for cardiac stimulation, one or more sensors including a first sensor 6 for provision of sensor data. The CIED 2 comprises a processing device 8 comprising a processor 10, a communication interface 12, memory 13, and a lead interface 14. The communication interface 12 comprises transceiver 12A and antenna 12B. The CIED 2 is configured for wireless communication with an accessory device 16 via the communication interface 12. The processor 10 is configured to obtain sensor data SD from the one or more sensors; determine a first set of first parameters based on the sensor data; determine a second set of second parameters based on the sensor data; determine a first cardiac event parameter indicative of a probability of a future cardiac event, wherein the first cardiac event parameter is based on one or more first parameters of the first set and one or more second parameters of the second set; determine if one or more transmission criteria are satisfied; and in accordance with a first transmission criterion being satisfied, transmit a first warning signal to accessory device 16, the first warning signal being indicative of the first cardiac event parameter.

Figure 2:
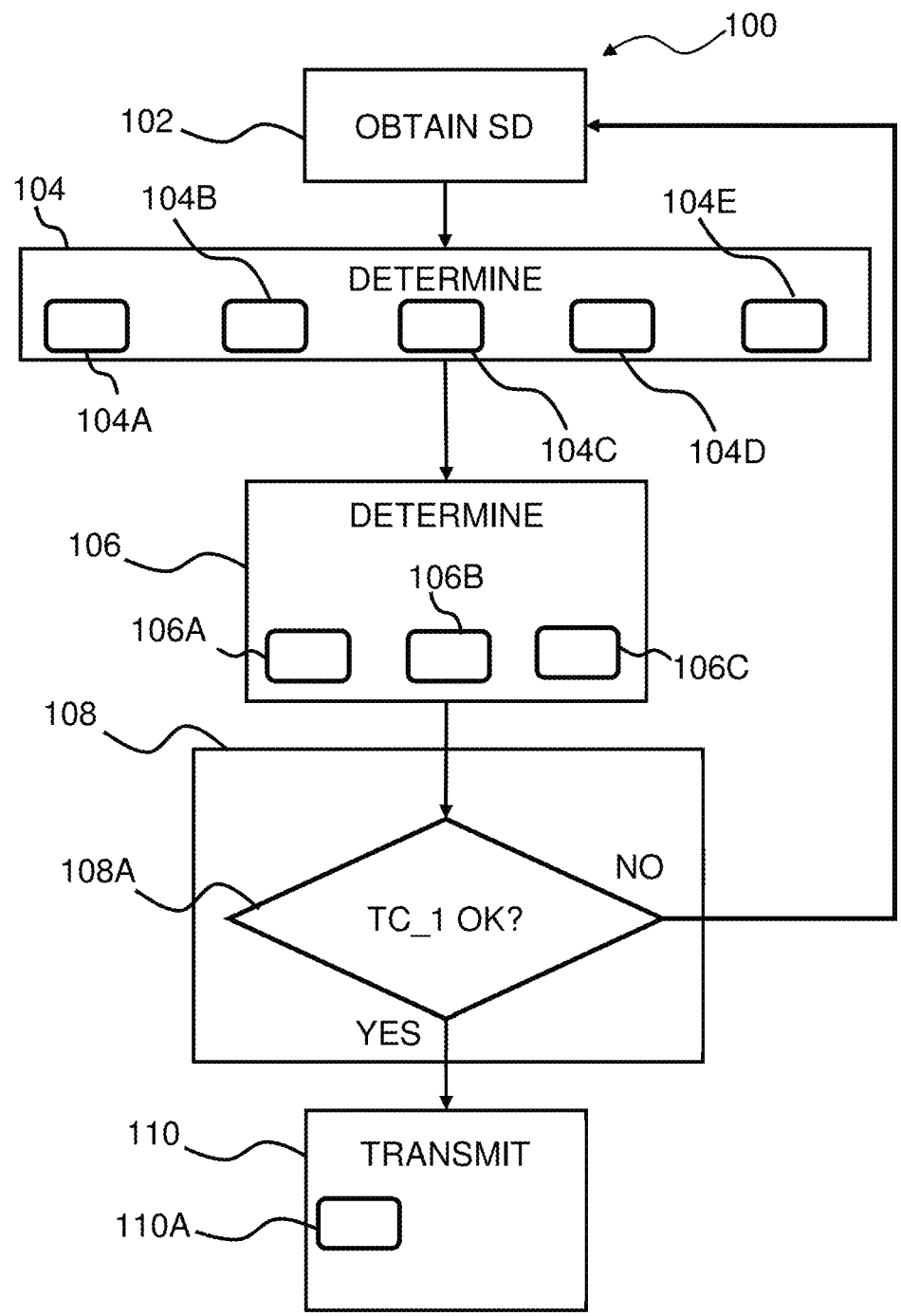
FIG. 2 is a flow diagram illustrating an exemplary method of the present disclosure, FIG. 3 schematically illustrates a block diagram of an exemplary processor of cardiovascular implantable electronic device.

FIG. 2 shows a flow chart of an exemplary method for cardiovascular event prediction. The method 100 for cardiovascular event prediction is optionally performed in a cardiovascular implantable electronic device, such as CIED 2, the method 100 comprising obtaining 102 sensor data SD from one or more sensors of one or more sensors of the cardiovascular implantable electronic device; determining 104 one or more sets of parameters P_1, . . . , P_N based on the sensor data. Determining 104 comprises determining 104A a first set P_1 of first parameters based on the sensor data and determining 104B a second set of second parameters based on the sensor data. The method proceeds to determining 106 one or more cardiac event parameters including determining 106A a first cardiac event parameter P_CE_1 indicative of a probability of a future cardiac event. Determining 106 one or more cardiac event parameters optionally includes determining 106B a second cardiac event parameter P_CE_2 indicative of a probability of a future cardiac event. Determining 106 one or more cardiac event parameters optionally includes determining 106C a third cardiac event parameter P_CE_3 indicative of a probability of a future cardiac event.

The first cardiac event parameter P_CE_1 is based on one or more first parameters of the first set P_1 and optionally one or more second parameters of the second set P_2.

The method 100 comprises determining 108 if one or more transmission criteria, such as a first transmission criterion TC_1 are satisfied, e.g. if P_CE_1>0.5. In accordance with first transmission criterion TC_1 being satisfied, the method 100 comprises transmitting 110A a first warning signal to an accessory device, the first warning signal being indicative of the first cardiac event parameter and/or the first cardiac event.

Figure 3:
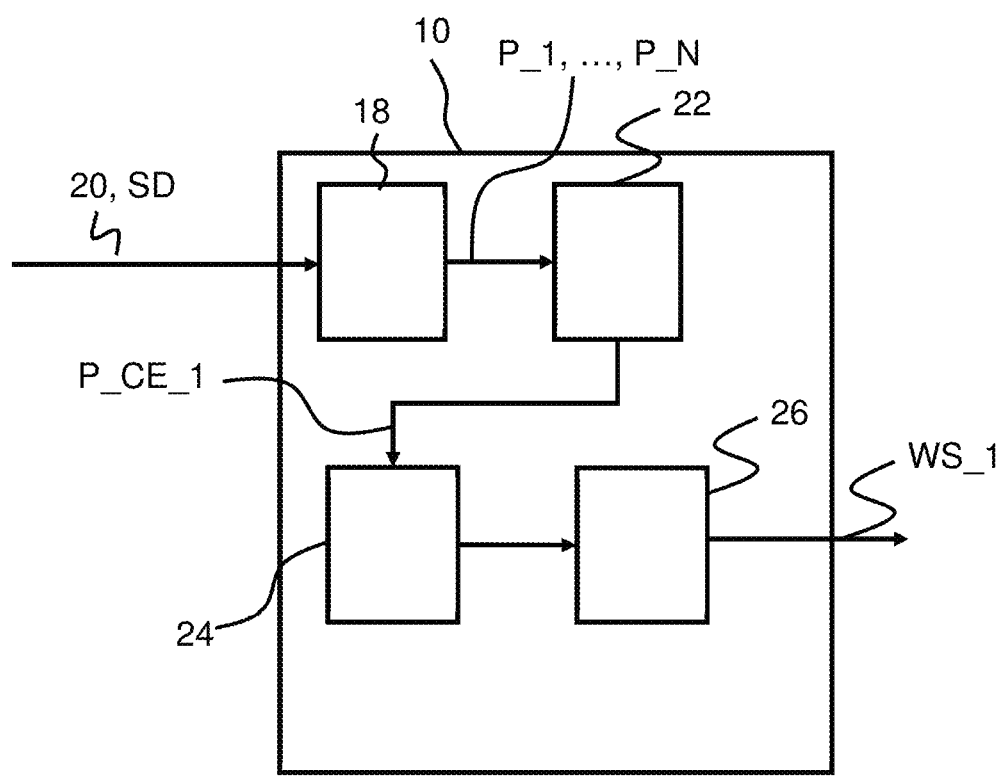

FIG. 3 shows a schematic block diagram of an exemplary processor 10 of processing device 8. The processor 10 comprises a parameter determination module 18 for determining one or more sets of parameters P_1, . . . _P_N based on sensor data 20 from the one or more sensors including first sensor 6 and/or from the memory 13. The processor 10 comprises cardiac event parameter determination module 22 for determining cardiac event parameter(s) based on the sets of parameters from the parameter determination module 18. The processor 10 comprises criterion module 24 for determining if one or more transmission criteria including a first transmission criterion TC_1 are satisfied. The processor 10 comprises transmission module 26 for, in accordance with the first transmission criterion being satisfied, transmitting, via communication interface 12, a first warning signal WS_1 to an accessory device, the first warning signal being indicative of the first cardiac event parameter and/or the first cardiac event.

Figure 4:
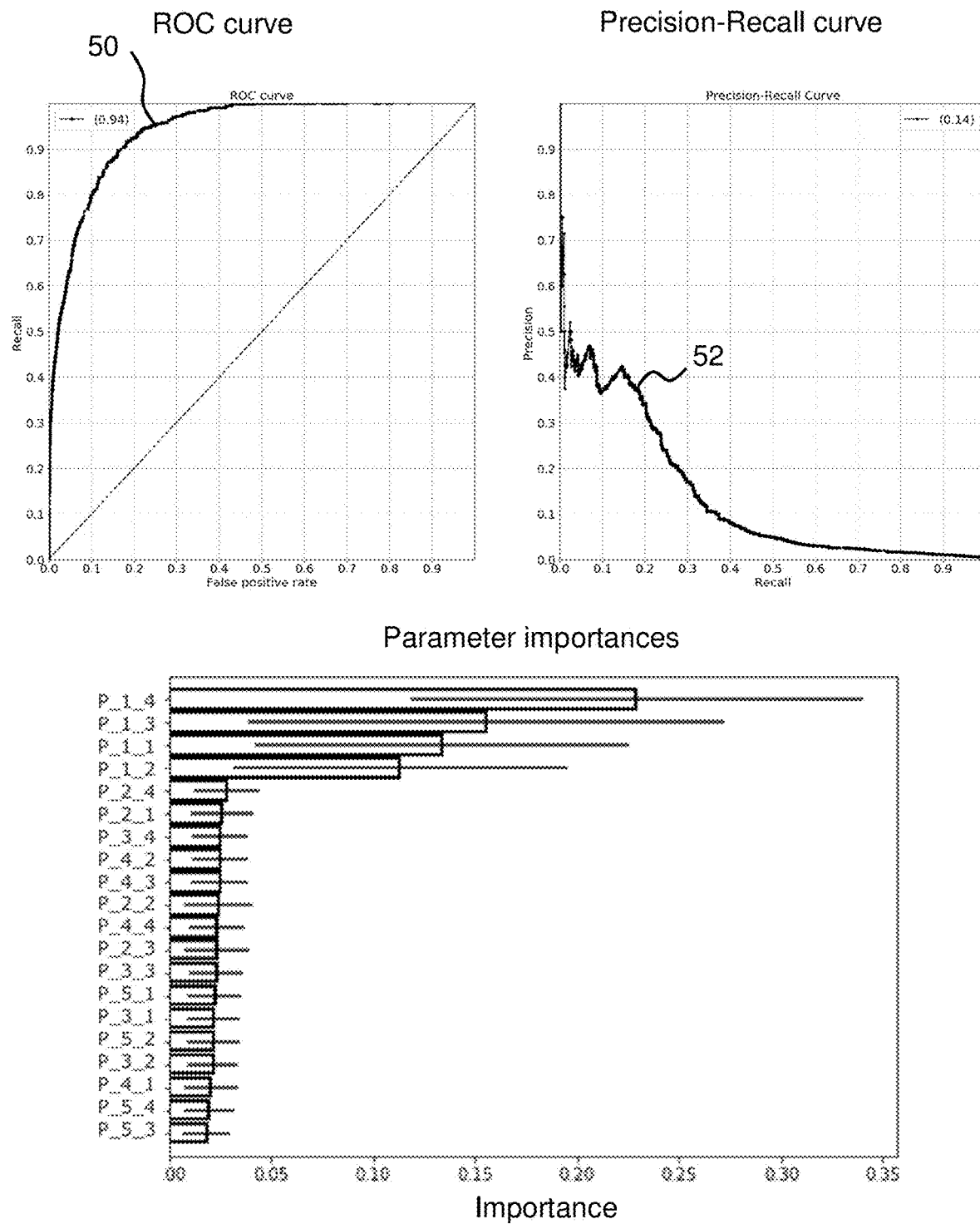
FIG. 4 shows exemplary results for VT/VF occurring within a day.

FIG. 4 shows exemplary results based on a random forest model for determining first cardiac event parameter indicative of first cardiac event (VT/VF) occurring within a day and shows ROC-curve, Precision-Recall curve, and parameter importance of predicting VT/VF based on first parameters (p_1_1 (CD), p_1_2 (CD-1), p_1_3 (CD-2), p_1_4 (CD-3)) indicative of heart rate during VTNF, second parameters (p_2_1 (CD), p_2_2 (CD-1, p_2_3 (CD-2), p_2_4 (CD-3)) indicative of average heart rate during daytime, third parameters (p_3_1 (CD), p_3_2 (CD-1), p_3_3 (CD-2), p_3_4 (CD-3)) indicative of activity, fourth parameters (p_4_1 (CD), p_4_2 (CD-1), p_4_3 (CD-3), p_4_4 (CD-3)) indicative of heart rate variability, and fifth parameters (p_5_1 (CD), p_5_2 (CD-1), p_5_3 (CD-2), p_5_4 (CD-3)) indicative of average heart rate during nighttime. The parameter importance shows the predictive power of each parameter. Concretely, FIG. 4 shows the importance of the following parameters according to the following ordered list of parameters (p_1_4, p_1_3, p_1_1, p_1_2, p_2_4, p_2_1, p_3_4, p_4_2, p_4_3, p_2_2, p_4_4, p_2_3, p_3_3, p_5_1, p_3_1, p_5_2, p_3_2, p_4_1, p_5_4, p_5_3). For example, the precision-recall curve illustrates that if a recall of 40% is chosen, then precision of about 10% is achieved. The results are based on a data set with 1,413,282 data points, spanning a time period from 1 Apr. 2007 to 31 Oct. 2014 on approximately 1,300 patients.

Figure 5:
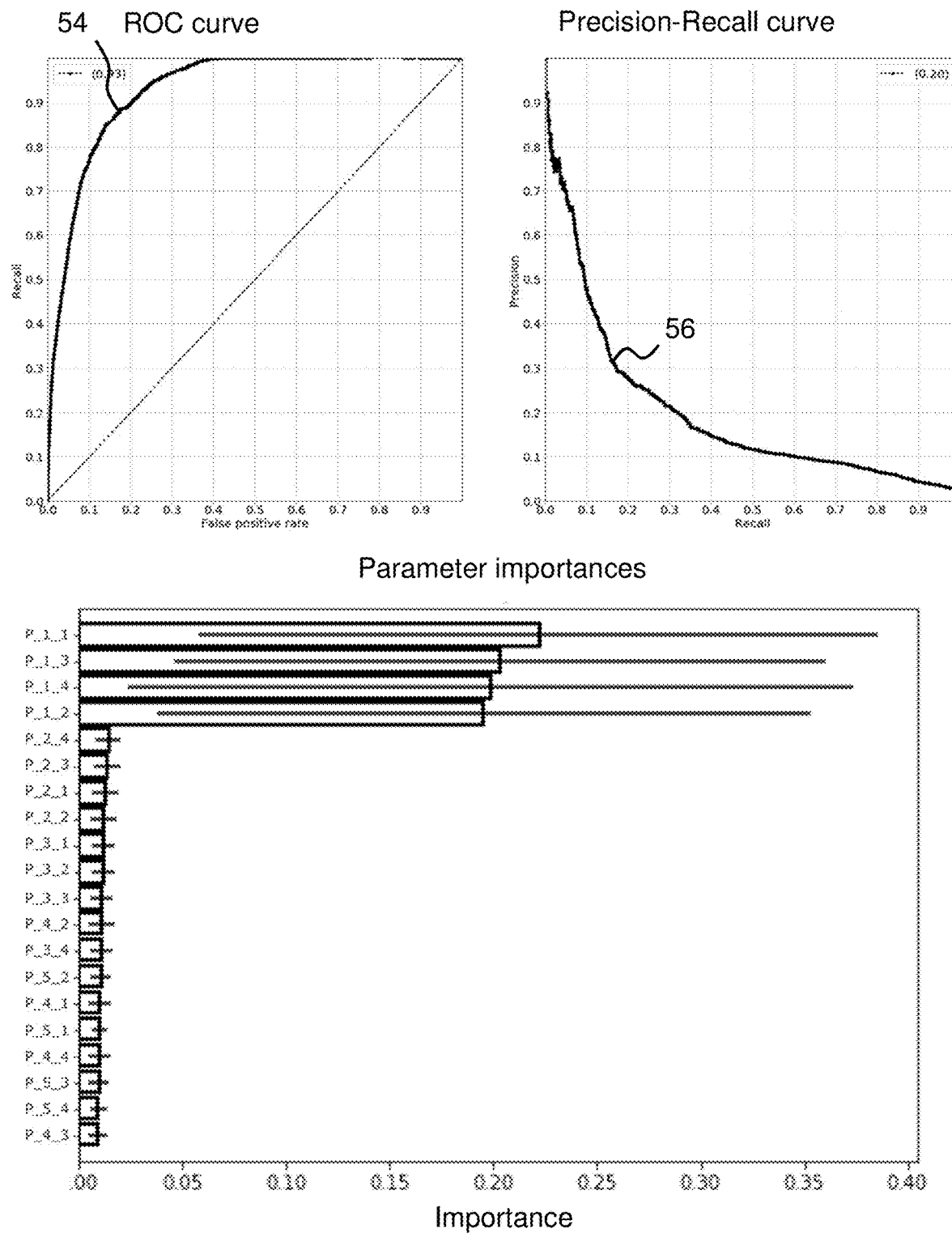
FIG. 5 shows exemplary results for VT/VF occurring within a week.

FIG. 5 shows exemplary results based on a random forest model for determining first cardiac event parameter indicative of first cardiac event (VT/VF) occurring within a week and shows ROC-curve, Precision-Recall curve, and parameter importance of predicting VT/VF within a week based on first parameters (p_1_1 (CD), p_1_2 (CD-1), p_1_3 (CD-2), p_1_4 (CD-3)) indicative of heart rate during VT/VF, second parameters (p_2_1 (CD), p_2_2 (CD-1, p_2_3 (CD-2), p_2_4 (CD-3)) indicative of average heart rate during daytime, third parameters (p_3_1 (CD), p_3_2 (CD-1), p_3_3 (CD-2), p_3_4 (CD-3)) indicative of activity, fourth parameters (p_4_1 (CD), p_4_2 (CD-1), p_4_3 (CD-3), p_4_4 (CD-3)) indicative of average heart rate during nighttime, and fifth parameters (p_5_1 (CD), p_5_2 (CD-1), p_5_3 (CD-2), p_5_4 (CD-3)) indicative of heart rate variability. The parameter importance shows the predictive power of each parameter. Concretely, FIG. 5 shows the importance of the following parameters according to the following ordered list of parameters (p_1_1, p_1_3, p_1_4, p_1_2, p_2_4, p_2_3, p_2_1, p_2_2, p_3_1, p_3_2, p_3_3, p_4_2, p_3_4, p_5_2, p_4_1, p_5_1, p_4_4, p_5_3, p_5_4, p_4_3). For example, the precision-recall curve illustrates that if a recall of 40% is chosen, then precision of about 15% is achieved. The results are based on a data set with 1,413,282 data points, spanning a time period from 1 Apr. 2007 to 31 Oct. 2014 on approximately 1,300 patients.

Figure 6:
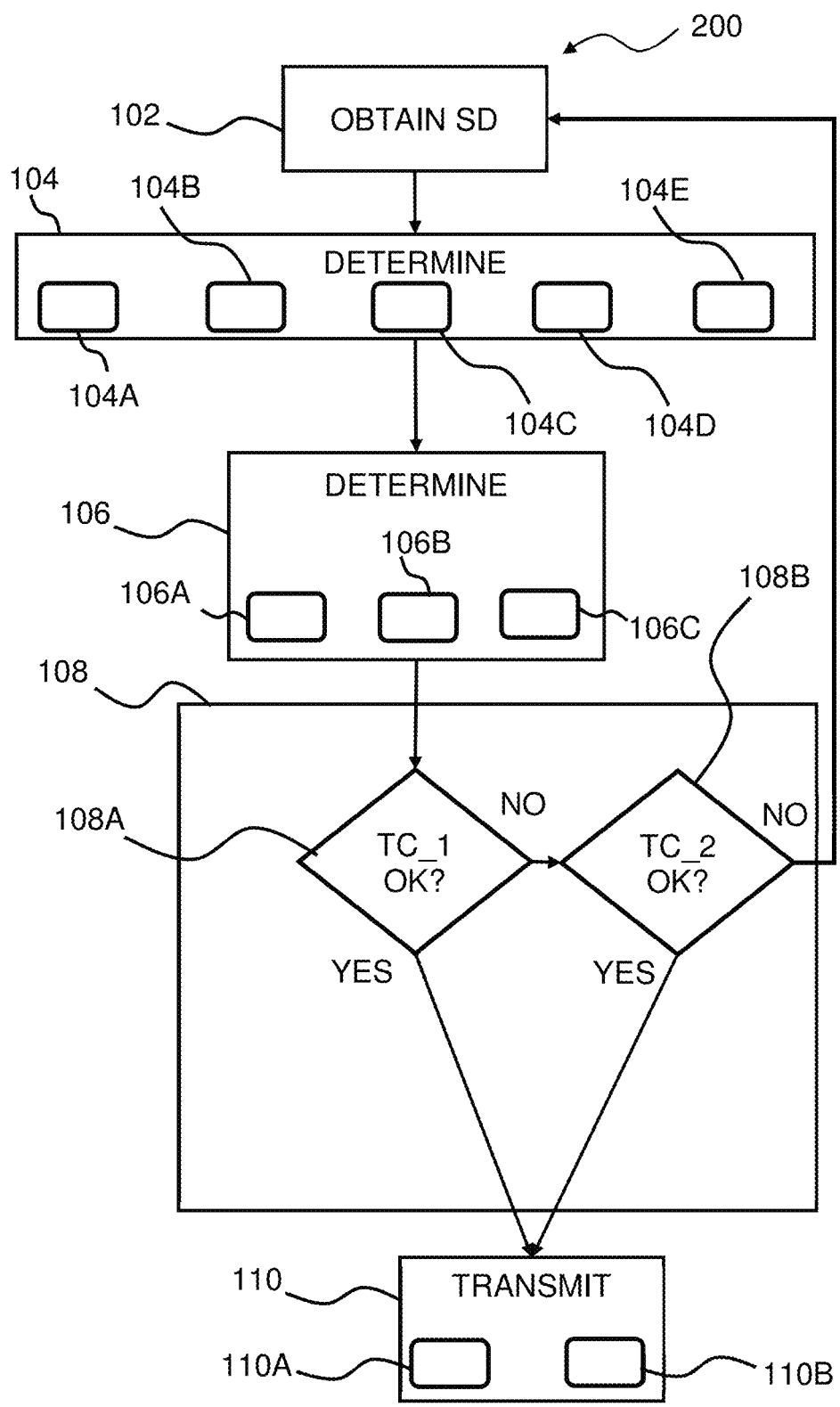
FIG. 6 is a flow diagram illustrating an exemplary method of the present disclosure.

FIG. 6 shows a flow chart of an exemplary method for cardiovascular event prediction. The method 200 for cardiovascular event prediction is optionally performed in a cardiovascular implantable electronic device, such as CIED 2, the method 200 comprising obtaining 102 sensor data SD from one or more sensors of one or more sensors of the cardiovascular implantable electronic device; determining 104 one or more sets of parameters P_1, . . . , P_N based on the sensor data. Determining 104 comprises determining 104A a first set P_1 of first parameters based on the sensor data and determining 104B a second set of second parameters based on the sensor data. The method proceeds to determining 106 one or more cardiac event parameters including determining 106A a first cardiac event parameter P_CE_1 indicative of a probability of a future cardiac event (first cardiac event) and determining 106B a second cardiac event parameter P_CE_2 indicative of a probability of a future cardiac event (first cardiac event or second cardiac event). The second cardiac event parameter P_CE_2 is based on one or more first parameters of the first set P_1 and optionally one or more second parameters of the second set P_2. The method 200 comprises determining 108 if one or more transmission criteria, such as a first transmission criterion TC_1 are satisfied 108A, e.g. if P_CE_1>0.5. In accordance with first transmission criterion TC_1 being satisfied, the method 200 comprises transmitting 110A a first warning signal to an accessory device, the first warning signal being indicative of the first cardiac event parameter and/or the first cardiac event. The method 200 comprises determining 108B if a second transmission criterion TC_2 is satisfied, e.g. if P_CE_2>0.5. In accordance with second transmission criterion TC_2 being satisfied, the method 200 comprises transmitting 110B a second warning signal to an accessory device, the second warning signal being indicative of the second cardiac event parameter and/or the associated cardiac event.

Disclosed are CIED's according to any of the following items.

Item 1. A cardiovascular implantable electronic device comprising:
 a first lead for cardiac stimulation;
 one or more sensors for provision of sensor data; and
 a processing device comprising a processor, a communication interface and a lead interface,
 wherein the processor is configured to:
 obtain sensor data from the one or more sensors;
 determine a first set of first parameters based on the sensor data;
 determine a first cardiac event parameter indicative of a probability of a future cardiac event, wherein the first cardiac event parameter is based on one or more first parameters of the first set;
 determine if one or more transmission criteria are satisfied; and
 in accordance with a first transmission criterion being satisfied, transmit a first warning signal to an accessory device, the first warning signal being indicative of the first cardiac event parameter.

Item 2. Cardiovascular implantable electronic device according to item 1, wherein the first transmission criterion is based on the first cardiac event parameter.

Item 3. Cardiovascular implantable electronic device according to any of items 1-2, wherein the processor is configured to determine a second set of second parameters based on the sensor data, and wherein the first cardiac event parameter is based on one or more second parameters of the second set.

Item 4. Cardiovascular implantable electronic device according to any of items 1-3, wherein the processor is configured to determine a third set of third parameters based on the sensor data, and wherein the first cardiac event parameter is based on one or more third parameters of the third set.

Item 5. Cardiovascular implantable electronic device according to any of items 1-4, wherein the processor is configured to determine a fourth set of fourth parameters based on the sensor data, and wherein the first cardiac event parameter is based on one or more fourth parameters of the fourth set.

Item 6. Cardiovascular implantable electronic device according to any of items 1-5, wherein the first cardiac event parameter is indicative of a probability of a first cardiac event occurring within a first time period of 15 minutes to 1 week.

Item 7. Cardiovascular implantable electronic device according to any of items 1-5, wherein the first cardiac event parameter is indicative of a probability of a first cardiac event occurring within a first time period of 12 hours to 24 hours.

Item 8. Cardiovascular implantable electronic device according to any of items 6-7, wherein the first cardiac event is electrical storm.

Item 9. Cardiovascular implantable electronic device according to any of items 6-7, wherein the first cardiac event is atrial fibrillation Item 10. Cardiovascular implantable electronic device according to any of items 6-7, wherein the first cardiac event is ventricular fibrillation/ventricular tachycardia.

Item 11. Cardiovascular implantable electronic device according to any of items 1-10, wherein the processor is configured to determine a fifth set of fifth parameters based on the sensor data, and wherein the first cardiac event parameter is based on one or more fifth parameters of the fifth set.

Item 12. Cardiovascular implantable electronic device according to any of items 1-11, wherein the processor is configured to:
   determine a second cardiac event parameter indicative of a probability of a future cardiac event, wherein the second cardiac event parameter is based on one or more first parameters of the first set; and
   in accordance with a second transmission criterion being satisfied, transmit a second warning signal to an accessory device, the second warning signal being indicative of the second cardiac event parameter.

Item 13. Cardiovascular implantable electronic device according to item 12, wherein the second cardiac event parameter is indicative of a probability of a second cardiac event occurring within a second time period.

Item 14. Cardiovascular implantable electronic device according to any of items 12-13, wherein the second cardiac event parameter is based on one or more second parameters of the second set.

Item 15. Cardiovascular implantable electronic device according to any of items 12-14, wherein the second cardiac event parameter is based on one or more third parameters of the third set.

Item 16. Cardiovascular implantable electronic device according to any of items 12-15, wherein the second cardiac event parameter is based on one or more fourth parameters of the fourth set.

Item 17. Cardiovascular implantable electronic device according to any of items 12-16, wherein the second cardiac event parameter is indicative of a probability of a second cardiac event occurring within a second time period of 15 minutes to 1 week.

Item 18. Cardiovascular implantable electronic device according to any of items 12-16, wherein the second cardiac event parameter is indicative of a probability of a second cardiac event occurring within a second time period of 12 hours to 24 hours.

Item 19. Cardiovascular implantable electronic device according to any of items 17-18, wherein the second cardiac event is electrical storm.

Item 20. Cardiovascular implantable electronic device according to any of items 17-18, wherein the second cardiac event is atrial fibrillation.

Item 21. Cardiovascular implantable electronic device according to any of items 17-18, wherein the second cardiac event is ventricular fibrillation/ventricular tachycardia.

Item 22. Cardiovascular implantable electronic device according to any of items 12-21, wherein the second cardiac event parameter is based on one or more fifth parameters of the fifth set.

Item 23. Cardiovascular implantable electronic device according to any of items 12-22, wherein the second transmission criterion is based on the second cardiac event parameter.

Item 24. Cardiovascular implantable electronic device according to any of items 1-23, wherein the first parameter(s) is/are indicative of heart rate.

Item 25. Cardiovascular implantable electronic device according to any of items 1-23, wherein the second parameter(s) is/are indicative of average heart rate.

Item 26. Cardiovascular implantable electronic device according to any of items 1-23, wherein the third parameter (s) is/are indicative of activity.

Disclosed are methods according to any of the following articles.

Article 1. Method for cardiovascular event prediction, the method comprising:
   obtaining sensor data from one or more sensors of one or more sensors of the cardiovascular implantable electronic device;
   determining a first set of first parameters based on the sensor data;
   determining a second set of second parameters based on the sensor data;
   determining one or more cardiac event parameters including a first cardiac event parameter indicative of a probability of a future cardiac event, wherein the first cardiac event parameter is based on one or more first parameters of the first set and one or more second parameters of the second set;
   determining if one or more transmission criteria are satisfied; and
   in accordance with a first transmission criterion being satisfied, transmitting a first warning signal to an accessory device, the first warning signal being indicative of the first cardiac event parameter.

Article 2. Method according to article 1, wherein the method is performed in a cardiovascular implantable electronic device.

Article 3. Method according to any of articles 1-2, wherein the first transmission criterion is based on the first cardiac event parameter.

Article 4. Method according to any of articles 1-3, the method comprising determining a second set of second parameters based on the sensor data, and wherein the first cardiac event parameter is based on one or more second parameters of the second set.

Article 5. Method according to any of articles 1-4, the method comprising determining a third set of third parameters based on the sensor data, and wherein the first cardiac event parameter is based on one or more third parameters of the third set.

Article 6. Method according to any of articles 1-5, the method comprising determining a fourth set of fourth parameters based on the sensor data, and wherein the first cardiac event parameter is based on one or more fourth parameters of the fourth set.

Article 7. Method according to any of articles 1-6, wherein the first cardiac event parameter is indicative of a probability of a first cardiac event occurring within a first time period of 15 minutes to 1 week.

Article 8. Method according to any of articles 1-6, wherein the first cardiac event parameter is indicative of a probability of a first cardiac event occurring within a first time period of 12 hours to 24 hours.

Article 9. Method according to any of articles 1-8, wherein the first cardiac event is electrical storm.

Article 10. Method according to any of articles 1-8, wherein the first cardiac event is atrial fibrillation.

Article 11. Method according to any of articles 1-8, wherein the first cardiac event is ventricular fibrillation/ventricular tachycardia.

Article 12. Method according to any of articles 1-11, the method comprising determining a fifth set of fifth parameters based on the sensor data, and wherein the first cardiac event parameter is based on one or more fifth parameters of the fifth set.

Article 13. Method according to any of articles 1-12, the method comprising:
determining a second cardiac event parameter indicative of a probability of a future cardiac event, wherein the second cardiac event parameter is based on one or more first parameters of the first set; and
in accordance with a second transmission criterion being satisfied, transmitting a second warning signal to an accessory device, the second warning signal being indicative of the second cardiac event parameter.

Article 14. Method according to article 13, wherein the second cardiac event parameter is indicative of a probability of a second cardiac event occurring within a second time period.

Article 15. Method according to any of articles 13-14, wherein the second transmission criterion is based on the second cardiac event parameter.

Article 16. Method according to any of articles 13-15, wherein the second cardiac event parameter is based on one or more second parameters of the second set.

Article 17. Method according to any of articles 13-16, wherein the second cardiac event parameter is based on one or more third parameters of the third set.

Article 18. Method according to any of articles 13-17, wherein the second cardiac event parameter is based on one or more fourth parameters of the fourth set.

Article 19. Method according to any of articles 13-18, wherein the second cardiac event parameter is indicative of a probability of a second cardiac event occurring within a second time period of 15 minutes to 1 week.

Article 20. Method according to any of articles 13-18, wherein the second cardiac event parameter is indicative of a probability of a second cardiac event occurring within a second time period of 12 hours to 24 hours.

Article 21. Method according to any of articles 19-20, wherein the second cardiac event is electrical storm.

Article 22. Method according to any of articles 19-20, wherein the second cardiac event is atrial fibrillation.

Article 23. Method according to any of articles 19-20, wherein the second cardiac event is ventricular fibrillation/ventricular tachycardia.

Article 24. Method according to any of articles 1-23, wherein the first parameter(s) is/are indicative of heart rate.

Article 25. Method according to any of articles 1-24, wherein the second parameter(s) is/are indicative of average heart rate.

Article 26. Method according to any of articles 1-25, wherein the third parameter(s) is/are indicative of activity.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labeling purposes only and are not intended to denote any specific spatial or temporal ordering. Furthermore, the labeling of a first element does not imply the presence of a second element and vice versa.

Although features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

LIST OF REFERENCES 2 cardiovascular implantable electronic device, CIED
4 first lead
6 first sensor
8 processing device
10 processor
12 communication interface
12A transceiver
12B antenna
13 memory
14 lead interface
16 accessory device
18 parameter determination module
20 sensor data
22 cardiac event parameter determination module
24 criterion module
26 transmission module
50 ROC curve for first cardiac event being VT/VF within a day
52 Precision-Recall curve for first cardiac event being VT/VF within a day
54 ROC curve for first cardiac event being VT/VF within a week
56 Precision-Recall curve for first cardiac event being VT/VF within a week
100, 200 method for cardiovascular event prediction
102 obtaining sensor data
104 determining one or more sets of parameter(s)
104A determining a first set of first parameter(s)
104B determining a second set of second parameter(s)
104C determining a third set of third parameter(s)
104D determining a fourth set of fourth parameter(s)
104E determining a fifth set of fifth parameter(s)
106 determining one or more cardiac event parameters
106A determining a first cardiac event parameter
106B determining a second cardiac event parameter
106C determining a third cardiac event parameter
108 determining if one or more transmission criteria are satisfied 108A first transmission criterion satisfied?
108B second transmission criterion satisfied?
110 transmitting warning signal(s) to an accessory device
110A transmitting a first warning signal to an accessory device
110B transmitting a second warning signal to an accessory device
SD sensor data
WS_1 first warning signal
WS_2 second warning signal

What is claimed is:

1. A cardiovascular implantable electronic device comprising:
a first lead for cardiac stimulation;
one or more sensors for provision of sensor data; and
a processing device comprising a processor, a communication interface and a lead interface,
wherein the processor is configured to:
obtain sensor data from the one or more sensors;
determine a first set of first parameters based on the sensor data, the first set including a first primary parameter based on current sensor data and a first secondary parameter based on sensor data earlier than the current sensor data;
determine a second set of second parameters based on the sensor data, the second parameters being different from the first parameters, the second set including a second primary parameter based on current sensor data and a second secondary parameter based on sensor data earlier than the current sensor data;
determine, based on a model, a first cardiac event parameter indicative of a probability of a future cardiac event and indicative of a probability of a first cardiac event occurring within a first time period of 15 minutes to 1 week from determining the first cardiac event parameter, wherein the first cardiac event parameter is based on one or more first parameters of the first set and one or more second parameters of the second set;
determine if one or more transmission criteria are satisfied; and
in accordance with a first transmission criterion being satisfied, transmit a first warning signal to an accessory device, the first warning signal being indicative of the first cardiac event parameter.

2. Cardiovascular implantable electronic device according to claim 1, wherein the first transmission criterion is based on the first cardiac event parameter.

3. Cardiovascular implantable electronic device according to claim 1, wherein the processor is configured to determine a third set of third parameters based on the sensor data and determine a fourth set of fourth parameters based on the sensor data, wherein the first cardiac event parameter is based on one or more third parameters of the third set and/or one or more fourth parameters of the fourth set.

4. Cardiovascular implantable electronic device according to claim 3, wherein the processor is configured to determine a fifth set of fifth parameters based on the sensor data, and wherein the first cardiac event parameter is based on one or more fifth parameters of the fifth set.

5. Cardiovascular implantable electronic device according to claim 3, wherein the third parameter is indicative of activity.

6. Cardiovascular implantable electronic device according to claim 1, wherein the first cardiac event is selected from electrical storm, atrial fibrillation, and ventricular fibrillation/ventricular tachycardia.

7. Cardiovascular implantable electronic device according to claim 1, wherein the processor is configured to:
determine a second cardiac event parameter indicative of a probability of a future cardiac event, wherein the second cardiac event parameter is based on one or more first parameters of the first set and one or more second parameters of the second set; and
in accordance with a second transmission criterion being satisfied, transmit a second warning signal to an accessory device, the second warning signal being indicative of the second cardiac event parameter.

8. Cardiovascular implantable electronic device according to claim 7, wherein the second cardiac event parameter is indicative of a probability of a second cardiac event occurring within a second time period.

9. Cardiovascular implantable electronic device according to claim 1, wherein the first parameter is indicative of heart rate.

10. Cardiovascular implantable electronic device according to claim 1, wherein the second parameter is indicative of average heart rate.

11. Cardiovascular implantable electronic device according to claim 1, wherein the first cardiac event is an electrical storm and the first time period is between 15 minutes to 12 hours.

12. Method, performed in a cardiovascular implantable electronic device, for cardiovascular event prediction, the method comprising:
obtaining sensor data from one or more sensors of the cardiovascular implantable electronic device;
determining a first set of first parameters based on the sensor data, the first set including a first primary parameter based on current sensor data and a first secondary parameter based on sensor data earlier than the current sensor data;
determining a second set of second parameters based on the sensor data, the second parameters being different from the first parameters, the second set including a second primary parameter based on current sensor data and a second secondary parameter based on sensor data earlier than the current sensor data;
determining, based on a model, a first cardiac event parameter indicative of a probability of a future cardiac event and indicative of a probability of a first cardiac event occurring within a first time period of 15 minutes to 1 week from determining the first cardiac event parameter, wherein the first cardiac event parameter is based on one or more first parameters of the first set and one or more second parameters of the second set;
determining if one or more transmission criteria are satisfied; and
in accordance with a first transmission criterion being satisfied, transmitting a first warning signal to an accessory device, the first warning signal being indicative of the first cardiac event parameter.

13. Method according to claim 12, wherein the first transmission criterion is based on the first cardiac event parameter.

14. Method according to claim 12, the method comprising:
determining a third set of third parameters based on the sensor data; and
determining a fourth set of fourth parameters based on the sensor data, wherein the first cardiac event parameter is based on one or more third parameters of the third set, and/or one or more fourth parameters of the fourth set.

15. Method according to claim 14, the method comprising determining a fifth set of fifth parameters based on the sensor data, and wherein the first cardiac event parameter is based on one or more fifth parameters of the fifth set.

16. Method according to claim 12, wherein the first cardiac event is selected from electrical storm, atrial fibrillation, and ventricular fibrillation/ventricular tachycardia.

17. Method according to claim 12, the method comprising:
- determining a second cardiac event parameter indicative of a probability of a future cardiac event, wherein the second cardiac event parameter is based on one or more first parameters of the first set and one or more second parameters of the second set; and
- in accordance with a second transmission criterion being satisfied, transmitting a second warning signal to an accessory device, the second warning signal being indicative of the second cardiac event parameter.

18. Method according to claim 17, wherein the second cardiac event parameter is indicative of a probability of a second cardiac event occurring within a second time period.

19. A cardiovascular implantable electronic device comprising:
- a first lead for cardiac stimulation;
- one or more sensors for provision of sensor data; and
- a processing device comprising a processor, a communication interface and a lead interface,
- wherein the processor is configured to:
- obtain sensor data from the one or more sensors;
- determine a first set of first parameters indicative of a heart rate of a patient based on the sensor data, the first set of first parameters including a first primary parameter based on current sensor data and a first secondary parameter based on sensor data earlier than the current sensor data;
- determine a second set of second parameters indicative of an average heart rate of the patient during a time period based on the sensor data, the second set of second parameters including a second primary parameter based on current sensor data and a second secondary parameter based on sensor data earlier than the current sensor data;
- determine a third set of third parameters indicative of the patient's level of activity during a time period based on the sensor data, the third set of third parameters including a third primary parameter based on current sensor data and a third secondary parameter based on sensor data earlier than the current sensor data;
- determine, based on a model, a first cardiac event parameter indicative of a probability of a future cardiac event and indicative of a probability of a first cardiac event occurring within a first time period of 15 minutes to 1 week from determining the first cardiac event parameter, wherein the first cardiac event parameter is based on one or more first parameters of the first set, one or more second parameters of the second set, and one or more third parameters of the third set;
- determine if one or more transmission criteria are satisfied; and
- in accordance with a first transmission criterion being satisfied, transmit a first warning signal to an accessory device, the first warning signal being indicative of the first cardiac event parameter.

* * * * *